(12) United States Patent
Klaming et al.

(10) Patent No.: US 9,906,780 B2
(45) Date of Patent: Feb. 27, 2018

(54) MEANS FOR CREATING AN AMBIENT EXPERIENCE

(71) Applicant: KONINKLIJKE PHILIPS N.V., Eindhoven (NL)

(72) Inventors: Laura Klaming, Utrecht (NL); Murray Fulton Gillies, Eindhoven (NL); Juergen Vogt, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 136 days.

(21) Appl. No.: 15/022,955

(22) PCT Filed: Sep. 22, 2014

(86) PCT No.: PCT/EP2014/070073
§ 371 (c)(1),
(2) Date: Mar. 18, 2016

(87) PCT Pub. No.: WO2015/044062
PCT Pub. Date: Apr. 2, 2015

(65) Prior Publication Data
US 2016/0234486 A1 Aug. 11, 2016

(30) Foreign Application Priority Data
Sep. 30, 2013 (EP) .................................. 13186744

(51) Int. Cl.
*H04N 13/00* (2006.01)
*H04N 13/04* (2006.01)
(Continued)

(52) U.S. Cl.
CPC ........ *H04N 13/0429* (2013.01); *A61M 21/00* (2013.01); *G01R 33/28* (2013.01);
(Continued)

(58) Field of Classification Search
CPC ........................... H04N 13/0429; A61M 21/00
(Continued)

(56) References Cited

U.S. PATENT DOCUMENTS

| 5,076,275 A | 12/1991 | Bechor et al. |
|---|---|---|
| 5,864,331 A | 1/1999 | Anand et al. |

(Continued)

FOREIGN PATENT DOCUMENTS

WO  2005120341 A1  12/2005

OTHER PUBLICATIONS

Melendez, J.C. et al., "Anxiety-related reactions associated with magnetic resonance imaging examinations". JAMA, 1993. 270(6): Abstract.
(Continued)

*Primary Examiner* — Jeffery Williams

(57) ABSTRACT

The invention relates to a system and a method for creating an ambient experience for a person, particularly for a patient to be examined in a medical imaging device having a bore into which a patient table can be moved. In a preferred embodiment, the system comprises a display (30) for displaying an image content such as a video for the relaxation of a patient, and an illumination device (40) for illuminating the surroundings with polarized light. Moreover, it comprises a viewing aid, particularly a pair of glasses (20), that is designed to at least partially block light from the illumination device (40) while letting light from the display (30) pass. The viewing aid (20) may for example comprise a polarization filter (23) that lets linearly polarized light (4) from the display (30) pass while blocking light from the illumination device (40) that is polarized in a perpendicular direction. A patient on the patient table can thus view the display (30) without being disturbed by an illumination of the surroundings.

11 Claims, 2 Drawing Sheets

(51) Int. Cl.
  *G01R 33/28* (2006.01)
  *A61M 21/00* (2006.01)
  *G01R 33/30* (2006.01)
  *A61B 5/055* (2006.01)
  *A61B 6/04* (2006.01)

(52) U.S. Cl.
  CPC ........... *G01R 33/283* (2013.01); *G01R 33/30* (2013.01); *H04N 13/0497* (2013.01); *A61B 5/055* (2013.01); *A61B 5/0555* (2013.01); *A61B 6/0407* (2013.01); *A61M 2021/005* (2013.01)

(58) Field of Classification Search
  USPC ........................................................ 348/53
  See application file for complete search history.

(56) References Cited

U.S. PATENT DOCUMENTS

| | | |
|---|---|---|
| 9,131,205 B2 | 9/2015 | Gillies et al. |
| 2010/0234722 A1 | 9/2010 | Trcka et al. |
| 2010/0238362 A1 | 9/2010 | Hughes et al. |
| 2012/0235884 A1 | 9/2012 | Miller et al. |
| 2013/0182085 A1* | 7/2013 | Ziarati .................. A61B 5/055 348/51 |
| 2013/0235168 A1 | 9/2013 | Gillies et al. |

OTHER PUBLICATIONS

Quirk, M.E., et al., "Anxiety in patients undergoing MR imaging". Radiology, 1989. 170(2): Abstract.

Katz, R.C. et al., "Anxiety and its determinants in patients undergoing magnetic resonance imaging". J Behav Ther Exp Psychiatry, 1994. 25(2): Abstract.

McIsaac, H.K., et al., "Claustrophobia and the magnetic resonance imaging procedure". J Behav Med, 1998. 21(3): Abstract.

Brennan, S.C.., et al., Anxiety and panic during magnetic resonance scans. Lancet, 1988. 2(8609): p. 512.

Minde, D.., Pinpointing moments of high anxiety during an MRI examination. Int J Behav Med, Jun. 2014, vol. 21, Issue 3, pp. 487-495.

* cited by examiner

MEANS FOR CREATING AN AMBIENT EXPERIENCE

CROSS-REFERENCE TO PRIOR APPLICATIONS

This application is the U.S. National Phase application under 35 U.S.C. § 371 of International Application No. PCT/EP2014/070073, filed on Sep. 22, 2014, which claims the benefit of European Patent Application No. 13186744.2, filed on Sep. 30, 2013. These applications are hereby incorporated by reference herein.

FIELD OF THE INVENTION

The invention relates to a system and a method for creating an ambient experience for a person. Moreover, it relates to a medical imaging system such as a CT or MRI scanning apparatus that comprises such a system.

BACKGROUND OF THE INVENTION

The WO 2005/120341 A1 discloses a system for enabling a patient to view images when undergoing medical treatment in an MRI (magnetic resonance imaging) scanner. Thus the patient shall be distracted and problems such as feelings of claustrophobia shall be reduced.

The WO 2012/066434 A1 discloses a method for displaying images on walls of an MRI scanner room. When a patient enters the scanner room, then an image is displayed on a wall visible to the patient, and when the patient is lying on a table of the scanner, then the projection of images is switched to another wall. Moreover, 3D images may be displayed via the projection of mutually displaced first and second images which are color or polarization coded.

The U.S. Pat. No. 5,864,331 discloses an MRI scanner with a display panel and LEDs that provide a patient undergoing an examination in the scanner with information about the remaining time of the scan and/or about states of the MRI procedure.

The U.S. Pat. No. 5,076,275 A discloses a viewing system for entertaining patients in an MRI scanner with television or VCR images.

SUMMARY OF THE INVENTION

In view of the above, it would be desirable to have a more robust means that allows for the creation of an ambient experience for a person, particularly a positive and/or relaxing ambient experience that can be used to prevent or at least reduce feelings of discomfort during medical examinations.

This object is addressed by a medical imaging system according to claim 1 and a method according to claim 2. Preferred embodiments are disclosed in the dependent claims.

A first aspect of the invention relates to a system for creating an ambient experience for a person, said system comprising the following components:

A display for displaying an image content.
An illumination device for illuminating the surroundings of the person.
A viewing aid for directing light from the display to the eyes of the person, wherein the viewing aid is designed to interact optically differently with light from the illumination device than with light from the display.

The "creation of an ambient experience" shall generally refer to a process or measure that affects the sensory perception a person has of his/her surroundings, particularly the optical and/or auditory perception. It typically comprises no actual physical rearrangement of objects in the surroundings of the person but rather other measures to affect or control the sensory input received by the person. One typical example of how an ambient experience can be created is the projection of images or colors, or the playback of sounds. In the above system, the creation of an ambient experience is particularly possible via the image content shown on the display.

The aforementioned "display" may be any device with a controllable visual appearance, for example a passive screen onto which images can be projected by a beamer, or an active monitor that is connected to an image source such as a video recorder or a computer. The mentioned beamer, video recorder and/or computer may optionally be considered as components of the system "display".

The term "image content" shall generally denote any visual information, comprising for instance monochrome colors, static images, text, and dynamic videos.

The illumination device may be any component that provides an illumination of a region where the person is or can be. The illumination is usually needed for practical reasons, for example in order to allow for a visual control of or a working in the surroundings of the person. The illumination will therefore typically be a given background experience rather than a specifically "created ambient experience".

The illumination device may particularly comprise means for emitting polarized light, e.g. a light source that immediately emits polarized light or a light source together with a polarization filter.

The term "viewing aid" shall denote any device, unit, or element that can be associated to the person to affect the way the person receives light from the surroundings. In a preferred embodiment, the viewing aid may for example comprise a pair of glasses or a mirror mounted in the vicinity of the person, e.g. attached to the MRI system.

The viewing aid is preferably designed such that light from the display is directed to the eyes of the person with preference over light from the illumination device. This means that, when a ray of display-light and a ray of illumination light fall onto the viewing aid from the same direction, a higher fraction of the ray of display-light is directed to the person than of the ray of illumination light.

According to a second aspect, an embodiment of the invention relates to a method for creating an ambient experience for a person, said method comprising the following steps:

Displaying image content.
Illuminating the surroundings of the person.
Directing light from displayed image content to the eyes of the person with preference over illumination light by interacting optically differently with illumination light than with light from the displayed image content.

The method comprises in general form the steps that can be executed with a system described above. Explanations provided for the system are therefore analogously valid for the method, too, and vice versa.

The system and the method allow for the creation of an ambient experience by displaying appropriate image contents that can be seen by a person via the viewing aid. At the same time, the surroundings of the person can be illuminated without severely disturbing this viewing of image content as it is passed to the person by the viewing aid with priority over the illumination. Thus it is for example possible that people in the surroundings of the person can be provided with sufficient light for working purposes.

In the following, various preferred embodiments of the invention will be described that can be realized in combination with both the system and the method.

According to one preferred embodiment, the viewing aid is designed to at least partially block illumination light while letting light from displayed image content pass. The blocked light may for example be absorbed by the viewing aid. The blocking of light from the illumination device by the viewing aid may be complete or partial. Similarly, light from the display may completely or partially be allowed to pass the viewing aid. In any case, the transparency of the viewing aid for light from the display is usually higher than its transparency for light from the illumination device or, to put it differently, light from the illumination device shall be blocked more than light from the display. The transparency for light from the illumination device may for example be about 20% (ideally 0%), while transparency for light from the display may be about 90% (ideally 100%). The light of the illumination device that is (at least partially) blocked may optionally be a specific part of the whole illumination light reaching the person, for example a part that has been reflected at a surface (e.g. the bore of an MRI scanner).

In another embodiment, the viewing aid is designed to at least partially reflect light from displayed image content. Preferably, the viewing aid directs display-light to the eyes of the person by this reflection. Furthermore, illumination light will not be reflected by the viewing or at least be reflected to a lesser extent than display-light. The above considerations on the blocking and passage of light are analogously valid for the reflection, too ("blocking" of illumination light corresponding to "non-reflection", "passage" of display-light to "reflection").

There are various ways how the viewing aid can interact optically differently with light from the illumination device ("illumination light") and light from the display ("display-light"), respectively. In one preferred embodiment, light from the illumination device has another polarization than light from the display. Light from the illumination device may for example be linearly polarized in a first direction while light from the display is linearly polarized in a second direction that is (approximately) perpendicular to the first direction. A polarization filter that is aligned with the second direction can then be used to let light from the display pass while light from the illumination device is blocked.

In another embodiment, light from the illumination device may have another spectral composition than light from the display. Preferably, the spectra of the illumination device and of the display may have no or only small overlap. A spectral filter can then be used to separate the two kinds of light.

To distinguish between light from the illumination device and from the display, the viewing aid may comprise a light filter, particularly a polarization filter that lets only light with a linear polarization in one particular direction pass.

The illumination device may optionally comprise a light source in combination with a light filter, particularly a polarization filter. The light source may then be any element that is convenient for generating light, for example a LED or an incandescent lamp, because the light filter guarantees that only light having desired characteristics (such as a polarization in a given direction) is emitted into the surroundings.

In a further development of the invention, the display may be designed to display 3D (three-dimensional) images, i.e. images that appear to be three-dimensional to a person when seen through the viewing aid. Different technologies are known and can be used for this purpose. Typically, these technologies comprise the simultaneous display of two images that show a scenario from two different perspectives, wherein the viewing aid guarantees that one of these images can only be seen by the left eye and the other only by the right eye. The different images may for example be coded in different colors, e.g. red and green, or have different polarizations. Appropriate filters in front of the eyes can then guarantee that each eye receives a different one of the images.

In all described embodiments, some audio content (music, text etc.) may optionally be played parallel to the displaying of image content. Thus the effect of the image content may be supported and extended.

According to a third aspect, an embodiment of the invention relates to a medical imaging system, particularly a Computed Tomography (CT) or Magnetic Resonance Imaging (MRI) apparatus, said system comprising the following components:

A patient table on which a patient can be disposed.

A scanning device with a bore into which the aforementioned patient table (carrying a patient) can be moved.

A system of the kind described above for creating an ambient experience for the patient, i.e. a system comprising a display for displaying an image content, an illumination device for illuminating the surroundings of the patient with polarized light, and a viewing aid for directing light from the display to the eyes of the patient, wherein said viewing aid is designed to interact optically differently with light from the illumination device than with light from the display based on the fact that illumination light has another polarization than light from the displayed image content.

The patient table may be any device on which a patient can be placed or seated and transported during a medical imaging procedure. It will typically comprise a horizontally oriented bed on which a patient can lie.

The "bore" of the scanning device will usually be are more or less narrow tunnel that completely surrounds the patient table with the patient. The narrowness of the bore often causes feelings of discomfort for the patient. In the described medical imaging system, this problem can be addressed by creating a relaxing ambient experience.

In the medical imaging system, the display will preferably be located such that the patient on the patient table can see it continuously or at least when the patient table is located in the bore of the scanning device.

The illumination device of the medical imaging system will usually be located such that the patient and his or her surroundings are illuminated sufficiently according to the needs of the medical staff that controls the imaging procedure.

Due to the constraints imposed by the scanning technology, the display can often not be located in the immediate viewing range of the patient. It is therefore possible to let the patient on the patient table wear a pair of glasses with prisms, mirrors or the like that allow for viewing "around the corner" and seeing the display that is arranged at a convenient place near the scanning device. Such a pair of glasses can additionally be used as the viewing aid, for example by providing it with appropriate light filters that discriminate between light from the illumination device and the display. Alternatively, a mirror mounted to the MRI system can be used as viewing aid.

In the medical imaging system, the illumination device may preferably comprise at least one light source at the entrance of the bore, i.e. at that end of the bore through which the patient table can be introduced into the bore. Additionally or alternatively, at least one light source may be located at the rear side of the bore, i.e. the end of the bore opposite to its entrance.

The light source(s) at the entrance of the bore may particularly comprise a light ring. The light source(s) at the rear side of the bore is/are usually needed to allow for a proper monitoring of the patient by the medical staff during the imaging procedure. The light sources should illuminate the interior of the bore as much as possible, thus reducing feelings of claustrophobia for a patient.

The light sources are prone to impair a proper viewing of the display. This problem is overcome with the system described above as the patient may wear a viewing aid that blocks light from the illumination device.

In a preferred further development of the medical imaging system, the displaying of image content on the display is synchronized with the movement of the patient table. This allows inter alia for a better control of the critical moment at which the patient is introduced into the bore of the scanning device. In particular, this movement of the patient table into the bore may at least partially be concealed by a proper synchronization with the display of the image content. The size and/or the location of the displayed image content may for example be adapted such that the movement of the patient is compensated, i.e. the patient gets no visual clues from the display about his or her own movement. For example, if the patient table is moved to come closer to the display, the size of the displayed image content may shrink accordingly such that it is seen under a constant viewing angle by a patient on the patient table.

In generalization of the aforementioned embodiment, an independent embodiment relates to a medical imaging system, particularly a CT or MRI apparatus, comprising:

a) A patient table on which a patient can be disposed.

b) A scanning device with a bore into which the patient table can be moved.

c) A display for displaying an image content, wherein the depiction of image content on the display is coupled to the position of the patient table such that the effect of the movement on the perception of displayed image contents by the patient is compensated for. When for example a still image of an object is displayed, the viewing angle of this object may remain constant for the patient.

BRIEF DESCRIPTION OF THE DRAWINGS

These and other aspects of the invention will be apparent from and elucidated with reference to the embodiments described hereinafter.

In the drawings.

Like reference numbers refer in the Figures to identical or similar components.

DETAILED DESCRIPTION OF EMBODIMENTS

One important component in an attempt to improve hospital environment as experienced by both staff and patients may be an audiovisual system created to lower the anxiety level of patients in the MR room. In an approach that is based on the "Ambient Experience" (AE), a theme video may be projected onto the wall, accompanied by audio and/or various LED lighting solutions which together create a total environment that is designed to relax the patient. Such an AE approach may also include other features such as rounded room corners to make the room appear seamlessly large, a design ethic that minimizes clutter, and a choice of theme (for which video and LED color is used) to create the feeling that the patient is in control of the environment. Besides these features of AE, the MR scanner itself may be equipped with a light ring at the entrance opening of the bore and two lights at the rear side of the scanner that illuminate the bore. The lights at the rear side of the MR scanner make the bore appear larger.

Various studies have shown that MRI examinations are associated with anxiety in many patients, which is mainly due to the narrowness of the bore and associated movement restrictions. Additionally, the length of the procedure and the loud noise of the scanner can cause anxiety. Up to 37% of all patients undergoing an MRI examination were found to experience moderate to high levels of anxiety and between 5% and 10% of patients were found to experience claustrophobia or panic. Being able to view the video projection when the table moves into the scanner, as well as from inside the bore itself can help to reduce anxiety and have a positive impact on the patient experience.

Figure 1:
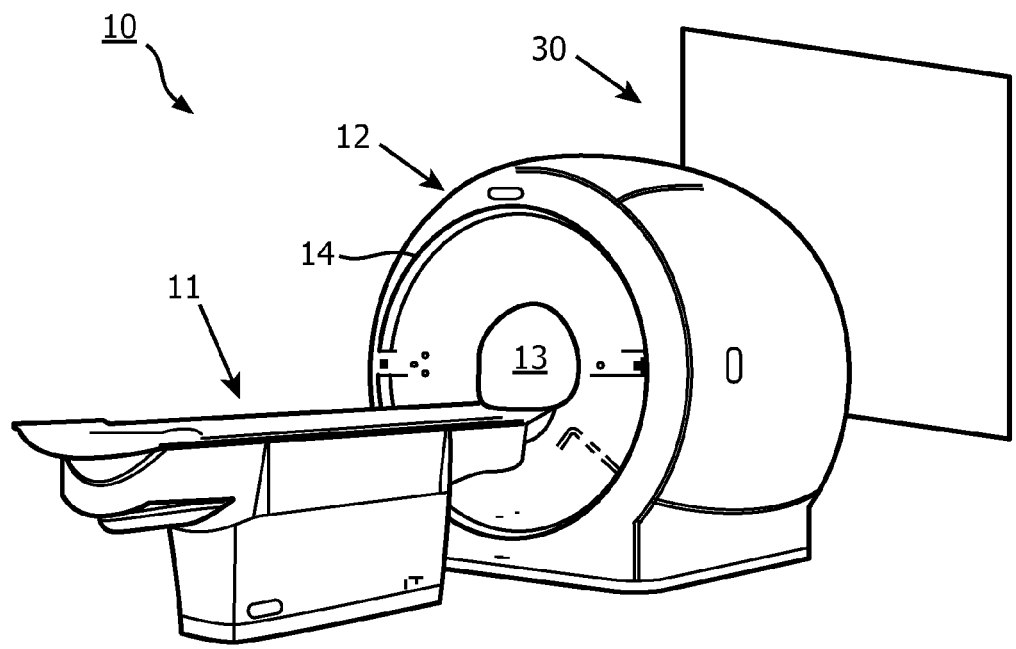
FIG. 1 shows a perspective front view of a medical imaging system according to an embodiment of the invention.
Figure 2:
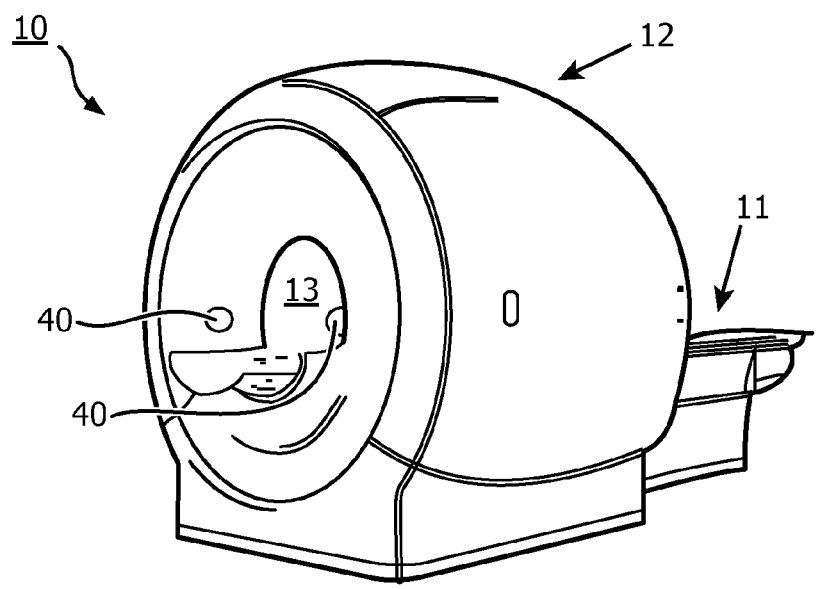
FIG. 2 shows the corresponding rear view of the imaging system of FIG. 1.

FIGS. 1 and 2 show a medical imaging system 10 with an MR scanner 12 that is equipped with an AE display 30 for a video projection. MR prism glasses 20 (FIG. 3) worn by the patient allow seeing of the room outside the bore while the patient lies on a patient table 11 inside the bore. With these glasses, the patient can see the video projection while the table 11 is moving into the bore as well as during the MRI examination.

Figure 3:
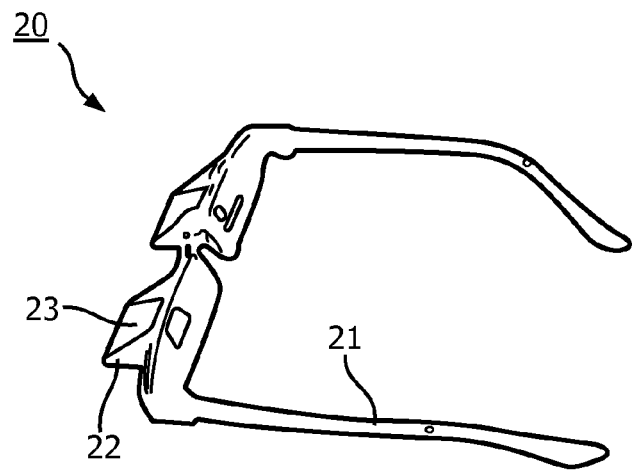
FIG. 3 shows a pair of glasses serving as a viewing aid.

FIG. 3 shows an example of MR prism glasses 20. They comprise earpieces 21 and a prism 22 in front of each eye. Moreover, a polarization filter 23 is attached to each prism.

As can be seen from FIG. 2, the MR scanner 12 is equipped with two "illumination devices" or lights 40 at the rear side which illuminate the bore 13 and make it seem larger, especially when the patient enters the MR room and while the table 11 moves into the scanner. Besides improving the patient experience, the light at the rear side of the scanner is required to enable the staff to see the patient during the examination and make sure he/she is calm during the entire examination as well as to remain in contact with the patient. The light sources 40 may be halogen lamps.

A problem of the described setup is that the tunnel light of the two lamps 40 at the rear side of the scanner may cause glare and prevent a patient from seeing the video projection when wearing the MR prism glasses and lying on the MR table. The lamps 40 cannot be switched off since they enable the staff to see the patient during the examination and to remain in contact with him/her as well making the bore appear larger which in turn improves the patient experience.

To decrease anxiety and enhance the patient experience while at the same time enabling the staff to see the patient during an MRI examination, the patient needs to wear MR prism glasses when the table moves into the bore and the lights at the rear side of the bore need to be switched on. In order to prevent glare, one proposal suggested here is to:

place a vertical polarizer immediately in front of the tunnel light 40;

replace the mirrors of the MR prism glasses 20 with mirrors that reflect horizontally polarized light but block vertically polarized light, and use an LCD screen 30 to show theme videos where the front polarizer is horizontal.

Figure 4:
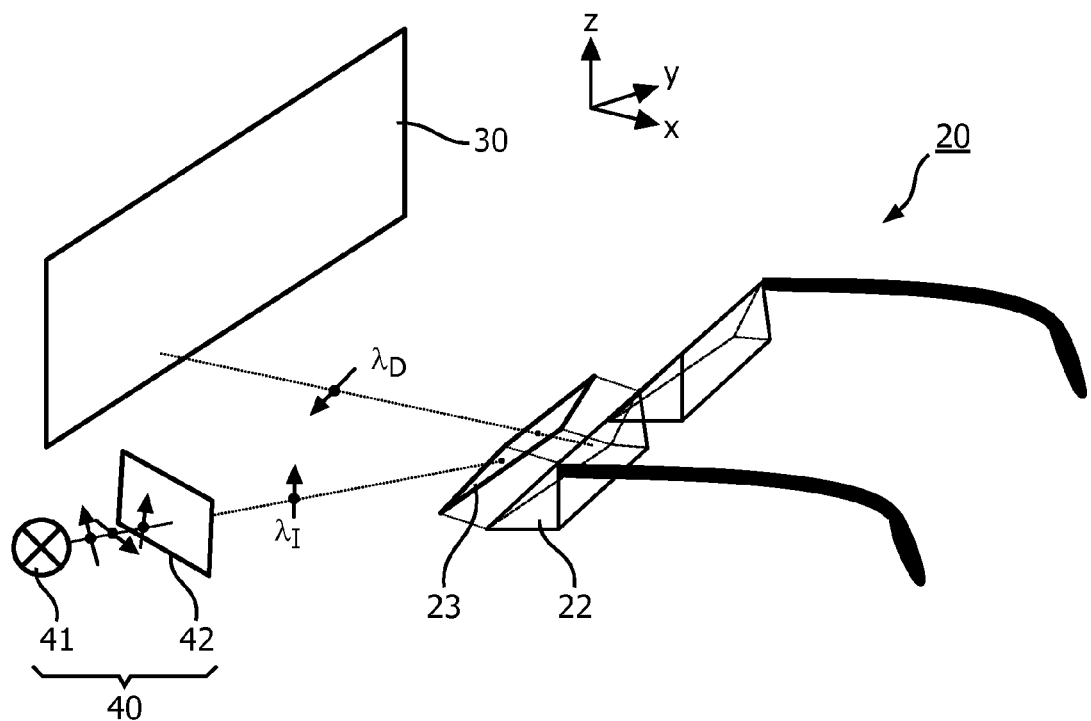
FIG. 4 schematically illustrates a system for creating an ambient experience according to an embodiment of the invention.

FIG. 4 schematically illustrates the described approach that makes use of a system for creating an ambient experience according to an embodiment of the invention. The system comprises the following components:

A "viewing aid", here realized by a pair of glasses 20 that can be worn by the patient and that allow for a viewing of the display 30 from within the bore 13. The viewing aid 20 comprises prisms 22 (and/or mirrors) in front of both eyes. Moreover, a linear polarization filter 23 is disposed in front of (or behind) said prisms, wherein one of these filters 23 is shown in a partially exploded view detached from the prism for purposes of illustration. In the shown example, the polarization filter 23 is arranged such that it allows for the passage of horizontally polarized light only (i.e. light polarized in x,y-direction of the associated coordinate system).

It should be noted that the polarization filters 23 may optionally be arranged on another facet of the prisms 22, for example on their bottom facets (with respect to FIG. 4), allowing for the viewing of a screen 30 at a perpendicular orientation to this facet.

The display 30 on which image contents such as still images or videos can be displayed. The display may for example be an LCD monitor, particularly a monitor with means that provide for the emission of polarized light. In the shown example, the light $\lambda_D$ emitted by the display 30 is polarized in horizontal x,y-direction and hence in alignment with the filter 23 of the viewing aid 20. Light from the display can therefore substantially unimpeded pass the polarization filter 23 and reach the patient's eyes.

An illumination device 40 comprising a light source 41 that emits unpolarized light and a polarization filter 42 that allows only for the passage of light $\lambda_I$ having a vertical polarization (z-direction). The linearly polarized light $\lambda_I$ of this light source is blocked by the filter 23 of the viewing aid and will hence not be seen by the patient. Accordingly, it cannot interfere with the viewing of the display 30.

The described approach enables the patient to wear the MR prism glasses 20 to see the video projection without glare when the patient table 11 moves into the scanner 12 and during the examination as the tunnel light will not be visible for the patient. The tunnel 13 will not appear dark to the patient as it is illuminated by the light ring 14 at its entrance and the illumination devices 40 at its rear side. The content on the LCD screen 30 will be fully visible via the glass and in fact have enhanced contrast as any diffuse light will be blocked by the polarization filter 23. The tunnel light will still provide the light that is required for the staff to see the patient during the MRI examination. When not wearing the MR prism glasses, the light source looks as usual which makes the bore appear larger when the patient enters the MR room.

It should be noted that the directions of polarization in FIG. 4 are only exemplary and can of course be changed, provided that the polarization directions of light from the illumination device and of light from the display are (substantially) perpendicular to each other. Moreover, other means for distinguishing the light could be used as well, for example a spectral filter that blocks light from the illumination device while letting light from the display pass.

In a further development of the above embodiment, polarizers for the MR prism glasses may be used to produce a 3D effect by projecting the same image into both eyes, but depicted from slightly different perspectives. The slightly different images are compared with each other in the visual cortex and the difference is used as a reference for depth. Because of creating an illusion of depth, 3D pictures are more appealing to viewers. Creating the illusion of more depth will make the video projection seem farther away and will make the MR room appear larger than it is. Furthermore, 3D content will be more engaging which is likely to have a number of positive consequences including less movement during the examination and a more positive patient experience.

In still another embodiment, 3D screen content can be displayed that creates the illusion of a bigger room. This can for example be done with perspective concepts from artworks.

The polarized glasses 20 already help to reduce anxiety, since the patients have less awareness of the medical process happening around them. Due to the high contrast, the patient focus is fully on the projection and stays distracted from the medical process. When using 3D visualization the patient can be even more immersed into the distracting elements.

However, once the patient table 11 starts moving into the scanner 12, the patient may get reminded of the medical procedure, since the view of the distractive scenes changes as soon as the patient is moved into the bore. Naturally, patients note when they are moved into the bore. From observations it is known that one of the most critical moments is when the patient is moved into the scanner.

To reduce the fear of entering the scanner, the polarized (or otherwise characterized) depiction of image content on the display 30 may be coupled to the position of the MR table 11. Once the table starts moving, the displayed (e.g. projected) video may change such that the patient has no visual trigger that the medical procedure is about to start. With this addition patients will have less notice of the medical procedure and stay immersed in the distraction provided.

In summary, an embodiment of the invention has been described that uses a polarized light source that is specially designed for the AE in-bore experience. The approach allows the operator to see clearly into the tunnel but does not cause glare for the patient and also does not decrease the contrast level of the video screen that can be viewed from the bore.

In a preferred embodiment, the proposed system comprises a display for displaying an image content such as a video for the relaxation of a patient, and an illumination device for illuminating the surroundings. Moreover, it comprises a viewing aid, particularly a pair of glasses, that is designed to at least partially block light from the illumination device while letting light from the display pass. The viewing aid may for example comprise a polarization filter that lets linearly polarized light from the display pass while blocking light from the illumination device that is polarized in a perpendicular direction.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A medical imaging system, particularly a CT or MRI apparatus, comprising:
   a) a patient table on which a patient can be disposed;
   b) a scanning device with a bore into which the patient table can be moved;
   c) a system for creating an ambient experience for a patient on the patient table, said system comprising:
      a display for displaying an image content;
      an illumination device for illuminating the surroundings of the patient with polarized light;
      a viewing aid for directing light from the display to the eyes of the patient, wherein said viewing aid is designed to interact optically differently with light ($\lambda_I$) from the illumination device than with light ($\lambda_D$) from the display based on the fact that illumination light ($\lambda_I$) has another polarization than light from the displayed image content.

2. The medical imaging system according to claim 1, characterized in that the viewing aid is designed to at least partially block illumination light ($\lambda_I$) while letting light ($\lambda_D$) from displayed image content pass.

3. The medical imaging system according to claim 1, characterized in that the viewing aid is designed to at least partially reflect light ($\lambda_D$) from displayed image content.

4. The medical imaging system according to claim 1, characterized in that the viewing aid comprises a pair of glasses or a mirror mounted in the vicinity of the patient.

5. The medical imaging system according to claim 1, characterized in that the illumination device comprises a light source and a light filter, particularly a polarization filter.

6. The medical imaging system according to claim 1, characterized in that the image content is displayed as one or more 3D images.

7. The medical imaging system according to claim 1, characterized in that the illumination device comprises at least one light source at the entrance of the bore and/or at least one light source at the rear side of the bore.

8. The medical imaging system according to claim 1, characterized in that displaying of the image content is synchronized with the movement of the patient table.

9. The medical imaging system according to claim 1, wherein the depiction of image content on the display coupled to the position of the patient table such that the effect of the movement on the perception of displayed image contents by the patient is compensated for by adaptation of the size and/or the location of the displayed image content.

10. A method for creating an ambient experience for a patient in a scanning device with a bore of a medical imaging system, said method comprising the following steps:
    displaying an image content;
    illuminating the surroundings of the patient with polarized light;
    directing light ($\lambda_D$) from displayed image content to the eyes of the patient with preference over illumination light ($\lambda_I$) by interacting optically differently with illumination light ($\lambda_I$) than with light ($\lambda_D$) from displayed image content based on the fact that illumination light ($\lambda_I$) has another polarization than light from the displayed image content.

11. The method according to claim 7, characterized in that the audio content is played parallel to the displaying of image content.

* * * * *